United States Patent [19]

Kolpak

[11] Patent Number: 4,924,695
[45] Date of Patent: May 15, 1990

[54] APPARATUS FOR COMPRESSING A FLUID SAMPLE TO DETERMINE GAS CONTENT AND THE FRACTION OF ONE LIQUID COMPOSITION IN ANOTHER

[75] Inventor: Miroslav M. Kolpak, Plano, Tex.

[73] Assignee: Atlantic Richfield Company, Los Angeles, Calif.

[21] Appl. No.: 340,607

[22] Filed: Apr. 19, 1989

Related U.S. Application Data

[63] Continuation-in-part of Ser. No. 281,421, Dec. 8, 1988, Pat. No. 4,852,395.

[51] Int. Cl.$^5$ ............................................. G01N 33/28
[52] U.S. Cl. ..................................... 73/61.1 R; 73/19
[58] Field of Search .................. 73/861.04, 61.1 R, 19

[56] References Cited

U.S. PATENT DOCUMENTS

| | | | |
|---|---|---|---|
| 3,246,145 | 4/1966 | Higgins | 73/61.1 R |
| 4,215,567 | 8/1980 | Vleck | 73/61.1 R |
| 4,429,581 | 2/1984 | Furmaga | 73/861.04 |
| 4,596,136 | 6/1986 | Zacharias | 73/61.1 R |

Primary Examiner—Hezron E. Williams
Attorney, Agent, or Firm—Michael E. Martin

[57] ABSTRACT

A multiphase fluid flow measuring system for measuring the volumetric fractions of gas, water and oil includes a housing having a bore in which a generally flexible tubular liner is disposed and forms with said housing a fluid displacement chamber. The liner together with portions of the housing defines a fluid sample chamber in which a sample of liquid is trapped by closable valves while a cylinder and piston hydraulic actuator displaces hydraulic fluid into the displacement chamber to reduce the volume of the sample chamber by deforming the liner. Pressure in the sample chamber is correlated with the change in volume of the sample chamber to determine residual gas content of the sample and/or the fraction of one known liquid in another known liquid.

8 Claims, 1 Drawing Sheet

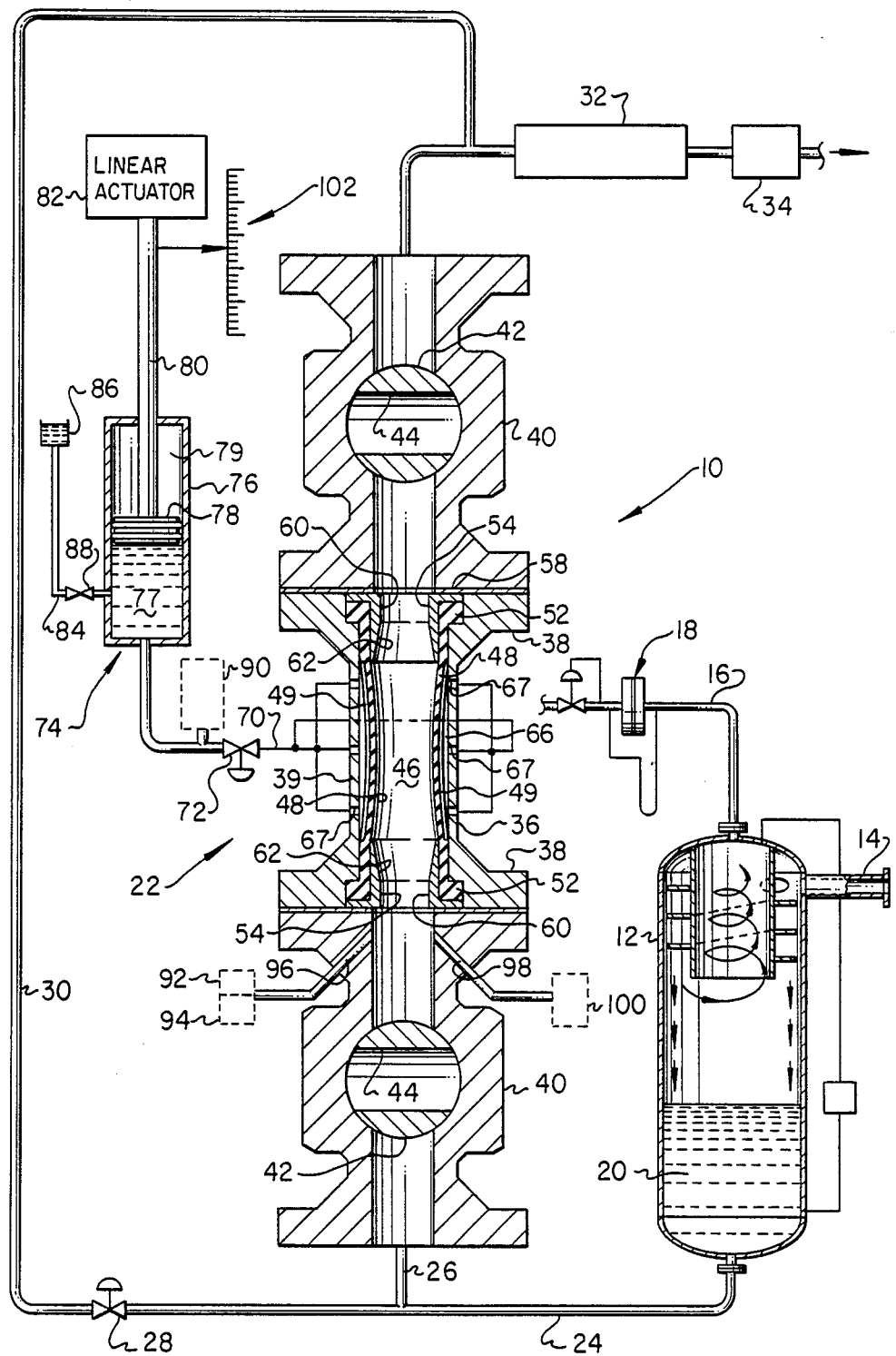

APPARATUS FOR COMPRESSING A FLUID SAMPLE TO DETERMINE GAS CONTENT AND THE FRACTION OF ONE LIQUID COMPOSITION IN ANOTHER

CROSS REFERENCE TO RELATED APPLICATION

This application is a continuation in part of prior co-pending application, Ser. No. 281,421 now U.S. Pat. No. 4,852,395 filed: Dec. 8, 1988 and entitled: Three Phase Fluid Flow Measuring System, which application is incorporated herein by reference.

BACKGROUND OF THE INVENTION

1. Field of the Invention

The present invention pertains to a three phase fluid flow measuring system including apparatus particularly useful for measuring the gas content and the water content in a gas-water-oil mixture and wherein the compressibility of a fluid sample is measured to determine the gas content and the water cut.

2. Background

The above-reference patent application discloses a system for measuring multiphase fluid flow, particularly mixtures of gas-water-hydrocarbon liquids. The system described in the reference application includes a sampling container which is closable to trap a predetermined quantity of liquid and into which a piston is movable to effect a decrease in the volume of the container chamber while raising the pressure of the liquid therein. This process may be used to measure the pressure/volume change and determine the residual gas content in the liquid as well as, with known liquid components, the fraction of one or more liquid compositions in the liquid. The use of a piston slidable in a cylinder to effect the volume change of the chamber presents certain maintenance and operational hazards and opportunities for error in the measurement process due to fluid leakage around the piston and trapping of bubbles of gas from previous samples of fluid being measured. The present invention overcomes these dificiencies as will be appreciated by those skilled in the art upon reading the following.

SUMMARY OF THE INVENTION

The present invention provides an improved system for measuring the residual gas content of a liquid sample and/or the composition of a liquid sample which includes known components such as a liquid mixture of oil and water.

In accordance with an important aspect of the present invention, there is provided a sampling device for use in a multiphase fluid flow measurement system which includes a sampling chamber defined at least in part by a flexible sleeve or liner member and which is displaceable by hydraulic fluid to effect compression of the fluid sample to be measured. In accordance with another important aspect of the present invention, a fluid sampling device is provided which is adapted to measure a known change in volume for a known pressure increase to determined the compressibility of a liquid sample and/or the residual gas content of the liquid sample by the displacement of a flexible sleeve or liner member by hydraulic fluid from a hydraulic cylinder and piston actuator and wherein the displacement of the piston of the actuator is measured to determine the change in volume of the sample held in the sampling chamber of the system.

The apparatus of the present invention as described generally hereinabove provides several advantages including isolation of the process fluid stream from any other fluids or potentially trouble prone apparatus used in changing the volume of the sampling chamber. Contents of the fluid sample being measured including solid particles and/or corrosive materials are isolated from those portions of an apparatus which might be subject to damage from such material. The likelihood of the process fluids being measured leaking to the exterior of the apparatus is substantially reduced and detection of leakage of the process fluid as well as the measuring fluid of the system is easily carried out.

Still further, the provision of the flexible liner reduces the probability of build up of scale and other debris on the interior surfaces of the structure defining the sampling chamber and the hydraulic systems used to compress the fluid in the chamber can be made arbitrarily "soft" to reduce the requirement for making a very small initial compression of the fluid to prevent overpressuring the sampling chamber in the event that the residual gas content of the liquid sample is relatively low or nil.

The above-mentioned features and advantages of the present invention together with other superior aspects thereof will be further appreciated by those skilled in the art upon reading the detailed description which follows.

BRIEF DESCRIPTION OF THE DRAWING

The drawing figure comprises a diagram in somewhat schematic form of the apparatus of the present invention.

DESCRIPTION OF A PREFERRED EMBODIMENT

The elements shown in the drawing figure may be in schematic form or out of scale in the interest of clarity and conciseness.

Referring to the drawing, there is illustrated a system for measuring the flow of a multiphase fluid stream and for determining the fraction of one or more components of the stream. In particular, the system illustrated, and generally designated by the numeral 10, is adapted for measuring the gas content and the water/oil fraction in a multiphase flowstream typically produced from hydrocarbon reservoirs. As described in the above-mentioned patent application, the system includes a primary gas separator vessel 12 for receiving a flowstream of a gas-liquid mixture through an inlet conduit 14 and wherein substantial separation of gas from the liquid composition is obtained. In the separator 12, the gas fraction separated from the liquid is conducted away by way of a conduit 16 and the flow rate may be measured by a suitable meter such as an orifice meter 18.

A liquid composition 20 retained in the separator vessel 12 is substantially free of gas, but may include a residual gas content of a few percent or more by volume. Typically, the liquid composition 20 is made up substantially of crude oil and produced water. In order to determine the residual gas content of the liquid composition 20 and to determine to the water/oil fraction of the liquid, it is conducted to a batch sampling apparatus, generally designated by the numeral 22, by way of a conduit 24 having a branch portion 26 leading directly to the apparatus 22. From time to time, a valve 28 may be closed to direct a sample of fluid to the apparatus 22 for measurement of the residual gas content and/or the water/oil fraction of the liquid composition. When a sample is not being measured, the liquid composition 20 is conducted by way of a conduit 30 to a suitable measurement device 32 which may be of a type described in the above-referenced patent application and a flowmeter 34 for measuring the flow rate of the composition itself. The apparatus 32 may, alternatively, be used to measure or confirm the water/oil fraction and may be of a type which measures the attenuation of microwave energy as caused by the dielectric properties of the liquid composition conducted through the apparatus 32.

The apparatus 22 is characterized by a generally tubular flanged housing 36 having opposed end flanges 38 which are connected to valve housings 40, respectively. The valve housings 40 comprise part of conventional rotary ball valve assemblies including ball type closure members 42 which are rotatable from the closed positions shown to an open through-flow position wherein fluid is conducted through respective ports 44 to and from a chamber 46 formed within the housing 36. The chamber 46 is defined in part by a flexible liner formed as a sleeve member 48 comprising an elongated cylindrical tubular portion 50 which may include opposed transverse flange portions 52 formed integrally therewith.

By way of example, the flange portions 52 fit within suitable annular recesses formed in the flanges 38 and are retained in the recesses by generally tubular flanged collar members 54 which are forcible insertable within the interior of the liner 48 to secure the liner to the housing 36. Each of the collar members 54 has a transverse flange portion 58 and a tubular collar portion 60 which is preferably tapered radially outwardly at 62 toward a transverse end opposite the flange portion 58. The collar members 54 are formed of a substantially rigid material and are sleeved within the tubular sleeve member 50 and retained in a position trapping the flange portions 52 of the sleeve member 48 when the housing 36 is assembled with the valve housings 40.

The cylindrical tube portion 50 of the sleeve 48 is adapted to be flexed radially inwardly with respect to the cylindrical tube portion 39 of the housing 36 to define a chamber 66 which may be occupied by a hydraulic fluid. The chamber 66 is in communication with a source of hydraulic fluid by way of a conduit 70 in which is interposed a control valve 72. The conduit 70 is connected to a hydraulic cylinder and the piston device 74 including a cylinder member 76 and a reciprocable piston 78 disposed therein for sliding movement. The piston 78 is suitably connected to a piston rod portion 80 which is connected to a linear actuator 82. Make-up hydraulic fluid is supplied to a chamber 77 formed in the cylinder 76 by way of a conduit 84 and a source 86. A suitable shut-off valve 88 is interposed in the conduit 84. A pressure transducer 90 is in communication with conduit 70 and suitable pressure and temperature transducers 92 and 94 are in communication with the chamber 46 by way of a passage 96. A calibration passage 98 is also provided in the valve housing 40 which includes the passage 96 for communication with a calibration apparatus 100.

A change in volume of the chamber 46 may be obtained with the valve member 42 in the closed position shown in the drawing figure by displacing hydraulic fluid with the piston and cylinder device 74 into the space or chamber 66 to cause the sleeve 48 to be displaced radially inwardly. This change in volume of the chamber 46 is proportional to the displacement of the piston 78 in the cylinder 76 and an equivalent volume change in the chamber 46 related to the movement of the piston 80 may be determined by a position scale or indicator generally designated by the numeral 102. The position scale 102 may be calibrated in units of volume change of the chamber 66 as related to linear movement of the piston rod 80 to displace hydraulic fluid into the chamber 66. A commercially available combined actuator and position indicator may be used such as a model X3155B-12 actuator with encoder manufactured by Industrial Device Corp., Novato, Calif.

The actuator 82 may be replaced by a hydraulic cylinder and piston-type fluid-displacing mechanism which would be characterized by a pump connected to the conduit 84 and interposed between the valve 88 and the source of liquid 86. A valve, not shown, would also be in communication with the conduit 84 and the chamber 79 of the cylinder 76. The aforementioned pump could be used to displace the piston to increase or reduce the volume of the chamber 77 and thus displace fluid with respect to the chamber 66. The piston rod 80 would be retained in some form and suitably connected to the position scale or indicator 102.

By way of example, the apparatus 22 may be sized such that the chamber 46 is approximately 12.0 inches in length and the inside diameter of the sleeve 48 is nominally approximately 2.0 inches. The overall length of the tubular member 36 is preferably about 12.0 inches. The tubular sleeve 48 is preferably formed of a Nitrile elastomer having a nominal wall thickness of the tubular portion 50 of approximately 0.10 inches. The valves 40 may be of a type commercially available and the housing member 36 may be of conventional construction for flow measuring equipment.

Assuming that the system 10 is being used to measure the flow rate of the gas, water, oil fractions of a multiphase composition, the system 10 would be operating on a substantially continuous basis to separate gas from the liquid mixture in the separator 12 and conducting the liquid mixture to the meters 32 and 34. Periodically, the valve 28 would be closed while the valve closure members 42 were moved to an open position to allow a sample of the liquid composition 20 to enter and fill completely the chamber 46. Simultaneous with closing of the valves 44 to the position shown in the drawing, the vale 28 would be reopened to bypass flow around the sampling apparatus 22.

Just prior to introducing a sample of liquid to be measured, the operating cycle would be conducted in a manner to slightly lower the pressure in the chamber 66 to assure that the sleeve 48 is firmly displaced in contact with the inside surface of the tubular portion 39 to establish the initial volume of the chamber 46. After this step, the valves 44 would be opened to flush any previous sample from the chamber 46 and then trap a new sample upon closure of the valves 44. With the new sample trapped in the chamber 46, the piston 78 is stroked to inject a measured amount of hydraulic fluid into the chamber 66 to effect reduction in volume of the chamber 46. This reduction in volume is read by the scale or indicator 102 and correlated with the pressure increase in the chamber 46 to determine the residual gas content of the liquid sample in accordance with the procedure described in the above-referenced U.S. patent application. This measurement cycle could be repeated as often as appropriate for satisfying any averaging for statistical purposes. Moreover, for a slowly varying process flowstream, a new sample might be analyzed on a selected time basis, i.e., from as low as one hour to as frequent as a thirty or sixty second cycle.

In order to assure complete evacuation of displacefluid from the chamber 66 prior to analyzing a sample, the inside surface of the housing 36 as well as the outer surface of the tubular liner 48 could be machined or otherwise formed to include small linear or spiral grooves which would promote uniform and complete evacuation of hydraulic fluid from the chamber 66. Alternatively, a fritted metal sleeve in the annulus chamber 66 could be implemented. In a preferred arrangement, the sleeve or liner 48 has opposed longitudinally extending grooves 49 formed in its outer surface, as shown. The conduit 70 is in communication with the chamber 66 by way of spaced apart ports 67 formed in the housing tube portion 39.

Several advantages are provided by the aforedescribed apparatus and process. The flexible tubular sleeve or liner isolates the process fluid from the measurement piston/actuating mechanism. Such things as chemical process streams, solid particles and/or corrosive material thus do not come in contact with conventional sealing elements such as o-rings, sliding, seals, or piston rings, and the like. A clean, isolated hydraulic fluid is the only fluid in contact with any of these types of components. Moreover, the likelihood of the process flowstream fluid leaking to the atmosphere is substantially reduced and would occur only if the sleeve 48 and/or the isolation valve 72 and the conduit 70 developed a leak. The valve 72 could be adapted to operate to close with the loss of hydraulic and/or electric power to the system 10. Automatic detection of fluid leakage on both sides of the valve 72 is possible. Fluid leakage between the valve 72 and the actuator 74 can be detected by closing the valve 72 and monitoring the pressure increase at the sensor 90 versus the displacement of the piston 78. Moreover, leakage into or out of the chamber 66 may be detected by opening the valve 72 and evacuating fluid out of the chamber 66 until pressure in the conduit 70 begins to drop. After this pressure drop is noted, if the pressure in the conduit then begins to rise, a leak typically could exist from the chamber 46 into the chamber 66 or leakage could be occurring from the atmosphere into the chamber 66. As mentioned previously, the provision of the liner 48 tends to reduce the likelihood of accumulation of solids or scale in the chamber 46.

Although preferred embodiments of the present invention has been described in detail herein, those skilled in the art will recognize that various substitutions and modifications may be made to the apparatus without departing from the scope and spirit of the invention as recited in the appended claims.

What is claimed is:

1. In a system for measuring a multiphase fluid flowstream including a water-oil-gas mixture:
separator means for separating the liquid phase of said flowstream from the gas phase, said separator means including a gas outlet conduit and a liquid outlet conduit; and
means for measuring the residual gas content of a liquid flowstream leaving said separator means through said liquid outlet conduit comprising:
a sampling apparatus including a housing section, valve means at opposite ends of said housing section and operable to be closed to define between said valve means a closed sample chamber in said housing section, a flexible liner disposed in said housing section and defining with said valve means said sample chamber and a fluid displacement chamber formed between said liner and said housing section, means for displacing fluid into said displacement chamber to cause said liner to reduce the volume of said sample chamber to determine the volumetric fraction of residual gas remaining in the sample trapped in said sample chamber.

2. The system set forth in claim 1 wherein:
said means for displacing fluid into said displacement chamber includes a cylinder and a piston reciprocably disposed in said cylinder to displace hydraulic fluid from said cylinder to said displacement chamber to effect displacement of said liner to reduce the volume of said sample chamber.

3. The system set forth in claim 2 including:
means for measuring the displacement of said piston to correlate the displacement of said piston with the reduction in volume of said sample.

4. The system set forth in claim 1 wherein:
said liner comprises a flexible tubular sleeve.

5. The system set forth in claim 4 wherein:
said sleeve includes at least one elongated groove formed in an outer surface of said sleeve in communication with said fluid displacement chamber and with port means formed in said housing section.

6. The system set forth in claim 1 wherein:
said housing section includes a generally elongated tubular section and opposed flanged portions at opposite ends of said tubular section, said liner includes a generally tubular liner portion and opposed flanged portions of said liner which are receivable in said flanged portions of said housing section, and a generally tubular collar means slidably insertably in said liner at opposite ends thereof for retaining said liner in said housing section.

7. The system set forth in claim 5 wherein:
said collar members include a tapered tubular portion insertable in said liner, respectively.

8. In a system for measuring at least one of the residual gas content and the fraction of one liquid in another of a multiphase fluid, an apparatus for determining the change in volume of a liquid sample of said fluid held in a closed sample chamber by comparing the change in volume with the increase in pressure in said sample chamber, said apparatus comprising:
an elongated tubular housing section having a generally cylindrical tubular portion defining a bore and opposed end portions of said housing section;
an elongated flexible tubular liner supported by said housing section in said bore and defining with said bore a displacement chamber, the interior of said liner defining in part a sample chamber for holding said liquid sample;
valve means connectable to said housing section at opposite ends thereof and defining with said liner said sample chamber;
a source of pressure liquid and positive displacement fluid displacement means including a conduit connected to said displacement chamber for displacing liquid into said displacement chamber to reduce the volume of said sample chamber by flexing said liner radially inwardly; and
means connected to said fluid displacement means for measuring the displacement of liquid into said displacement chamber to determine the volume change of said sample chamber as a function of the fluid pressure change in said sample chamber to determine at least one of the residual gas content and fraction of one liquid in another in said liquid sample.

* * * * *